United States Patent [19]

Baron et al.

[11] Patent Number: 4,627,424
[45] Date of Patent: * Dec. 9, 1986

[54] COLD WATER CURABLE ORTHOPEDIC CAST

[75] Inventors: Kenneth S. Baron, San Ramon; David W. Wood, San Francisco, both of Calif.

[73] Assignee: Hexcel Corporation, San Francisco, Calif.

[*] Notice: The portion of the term of this patent subsequent to Jan. 24, 2001 has been disclaimed.

[21] Appl. No.: 502,280

[22] Filed: Jun. 8, 1983

Related U.S. Application Data

[63] Continuation-in-part of Ser. No. 322,657, Nov. 18, 1982, Pat. No. 4,427,002.

[51] Int. Cl.$^4$ ............................................... A61F 5/04
[52] U.S. Cl. .................................... 128/83; 128/91 R; 528/75
[58] Field of Search .................... 128/81, 82, 82.1, 83, 128/90; 528/75, 45, 59

[56] References Cited

U.S. PATENT DOCUMENTS

| | | | |
|---|---|---|---|
| 3,787,272 | 1/1974 | Nisbet | 128/90 |
| 4,306,549 | 12/1981 | Canie | 128/90 |
| 4,427,002 | 1/1984 | Baron et al. | 128/83 |

Primary Examiner—Richard J. Apley
Assistant Examiner—David J. Isabella
Attorney, Agent, or Firm—Oblon, Fisher, Spivak, McClelland & Maier

[57] ABSTRACT

A bandage material for forming in place an orthopedic cast comprising a pliant, large mesh fabric carrier formed from a knit of a high-strength, high-modulus fiberglass yarn with a low moisture pick-up, the fabric carrier having openings of relatively large transverse dimension, and being coated with a polymer composition comprising a cold water curable polyurethane prepolymer comprising the reaction product of a polyalkylene ether diol, a polyalkylene ether triol and a diisocyanate.

9 Claims, 3 Drawing Figures

COLD WATER CURABLE ORTHOPEDIC CAST

CROSS-REFERENCE INFORMATION

This application is a continuation-in-part of copending U.S. patent application Ser. No. 322,657, filed Nov. 18, 1982, now U.S. Pat. No. 4,427,002 issued Jan. 27,1984 which is incorporated by reference herein.

BACKGROUND OF THE INVENTION

Field of the Invention

This invention relates to a cold water curable orthopedic cast forming material in the form of a bandage.

Orthopedic structures find wide use in the immobilization of limbs in aid of the healing process. In the maintenance of fixation of fractured bones, immobilization of inflamed or injured joints, in cases of disease or trauma, and for the support and immobilization of ligamentous and muscular structures in instances of strains and sprains, it is necessary to encase the limb in a partially or completely surrounding rigid form or cast. The immobilized limb may be encased in such rigid structure for long periods of time, frequently as much as six weeks or more.

There are two major considerations for a cast. The first consideration concerns the formation of the cast. A satisfactory cast material should be easily handleable, should not have properties which deleteriously affect the limb, particularly, the skin, should have a reasonable setting time or work life, so as to allow a reasonable period of time in which to mold the cast material about the limb, should be flexible during application to the limb so as to readily assume the shape of the limb, should be free of offensive or noxious solvents or other such chemicals, and should set within a relatively short time under relatively mild conditions. In addition, it is desirable that a minimuym of equipment should be involved in formation of the cast. Also, it is desirable that during the forming of the cast the material does not generate an uncomfortable exothermic reaction, and that upon drying, curing or setting up it has a negligible shrinkage factor.

The second consideration concerns the properties of the cast after it is formed. Desirably, the cast should be of a lightweight material so as to minimize the inconvenience to the wearer, porous so as to allow the underlying skin to breathe and not become macerated or otherwise irritated, should have sufficient structural strength so as to retain its structure under normal usage, should be sufficiently sturdy to maintain the joint or limb in the immobilized position and protect the joint or limb from jars, and should be easily removable. An optimum cast should also be waterproof, i.e. the coated fabric material itself should not absorb and retain water, be as X-ray transparent as possible, and be highly impact and abrasion resistant.

In this regard, U.S. Pat. No. 2,711,168 discloses a cast-forming element comprising a base warp knit fabric and plaster of Paris coated thereon; U.S. Pat. No. 3,048,169 discloses the formation of casts by reacting ingredients in an impermeable envelope to form a thermoplastic resin and then shaping the resin about the limb; U.S. Pat. No. 3,301,252 discloses the formation of casts by spraying a foamable composition over the affected area of the limb and allowing a solidified foam to form; U.S. Pat. No. 3,630,194 discloses cast formation using a bandage material supporting a solid, water-soluble vinyl monomer, dipping the same into water in the presence of a catalyst for polymerization, wrapping the limb with the bandage and allowing polymerization to take place; U.S. Pat. No. 3,631,854 discloses cast formation using an inflatable, double-walled sleeve which is placed about the affected limb, filled with a liquid, curable composition, and then allowed to harden; U.S. Pat. No. 3,787,272 discloses an air-permeable, glass fiber fabric for use in orthopedic casts; U.S. Pat. No. 3,882,857 discloses an orthopedic cast comprising an inner protective sleeve and an outer immobilizing structure; U.S. Pat. No. 4,105,025 discloses a method of cast formation wherein a bandage impregnated with a crystallizable polyurethane is heated above the melting point of the polyurethane, wrapping the affected body member with the bandage and then allowing the same to cool and thereby crystallize or harden; U.S. Pat. No. 4,131,114 discloses cast formation using package containing a carrier material and in separate compartments the reactive components necessary to form a curable resin, wherein for application the reactive components must be brought together, impregnated into the bandage, excess removed and then the bandage must be applied to the affected limb and allowed to cure; U.S. Pat. No. 4,215,684 discloses a net bandage comprising elastic and non-elastic fibers; and German Offenlegungschrift No. 2,651,089 discloses a bandaging material comprising a fabric impregnated and/or coated with a prepolymer which is the reaction product of at least one aromatic polyisocyanate and at least one polyol containing tertiary amino nitrogen.

Because of the numerous and varied requirements for an orthopedic cast material, none of the presently known immediately available cast materials provide all or substantialkly all of the properties indicated above.

A need, therefore, continues to exist for a cast material which is strong and thin, drapable, not abrasive, easy to cut, having a low exotherm, exhibits good breathability, is X-ray transparent and has a good package shelf life.

SUMMARY OF THE INVENTION

Accordingly, one object of the invention is to provide a bandage material for forming in place an orthopedic cast which is strong and thin, drapable, not abrasive, easy to cut, has a low exotherm upon setting, exhibits good breathability, is X-ray transparent and has a good package shelf life.

Another object of the present invention is to provide a bandage material for forming in place an orthopedic cast which has a good shelf life, a low exotherm upon setting, and when set exhibits high porosity, good strength and good impact resistance.

A further object of the present invention is to provide a bandage material for forming in place an orthopedic cast which balances the competing needs of high porosity with interlaminar bonding surface area; reasonable curing times which require highly reactive systems with low exotherms and long shelf life; and high impact strength with a high Young's modulus.

Briefly, these objects and other objects of the invention, as hereinafter will become more readily apparent, can be attained by providing a bandage material for forming in place an orthopedic cast comprising a pliant, large mesh fabric carrier formed from a knit of a high-strength, high-modulus fiberglass yarn with a low moisture pick-up, the fabric carrier having openings of relatively large transverse dimension, and being coated with a polymer composition comprising a cold water curable polyurethane prepolymer comprising the reaction product of a polyalkylene ether diol, a polyalkylene ether triol and a diisocyanate.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

A highly advantageous material is provided for forming orthopedic casts. A fabric web is employed having relatively large openings and relatively heavy strands. Preferably, the strands are of a loose weave or knit, so as to allow at least partial impregnation, as well as coating, by the polymeric material. The web carrier serves as a structural element in the final product, coated with the polymeric composition.

In describing the present invention, the elements of the invention will be described as follows: (1) the carrier material; (2) the polymeric composition; (3) a method of preparing the orthopedic cast forming bandage; and (4) the orthopedic cast forming bandage.

Carrier Material

Figure 1:
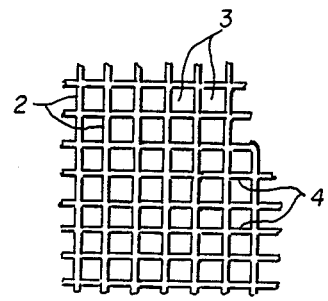
FIG. 1 is a partial view of a knit carrier before impregnation with the resin according to this invention.

Referring to FIG. 1, the carrier material is a flexible large mesh fabric, preferably knit, defining a lattice of relatively large openings, 3. The smallest dimension of the openings will generally be at least 0.015 sq. in. and preferably a minimum of 0.022 sq. in., about 0.034 sq. in. and generally not exceeding 0.25 sq. in., more usually not exceeding 0.050 sq. in. The openings may be of any configuration, such as square, rectangular, polygonal, or the like. The opening is large enough so that in the finished product the polymer composition preferably does not form air impervious windows across the openings. The strands, 2, of the carrier which define the openings are relatively heavy yarn or 400–1500 denier, preferably 500–1000 denier, most preferably 840–1000 denier.

Materials which may be used include fiberglass polyester, nylon and polypropylene. Fiberglass is a particularly preferred material in view of its low cost, wide availability, and ease of use. Generally, any type of fiberglass having sufficient strength may be used.

By way of more specific example, a knit of the Raschel type inherently provides a highly flexible carrier material. Such a preferred knit is shown in FIG. 2, wherein the fabric is comprised of walewise parallel chains and filling threads having sinuous configuration looped between said chains, said fill thread loops being formed around a link of one of said chains and then around a link of another of said chains, each loop of each fill thread being in a course difference from the course in which the other loopings thereof occur and the loops of different fill threads in the same course pointing in the same direction, said fabric being substantially unstretchable in the walewise direction, but substantially stretchable in the direction normal thereto, the fabric containing not more than 20 wales per inch width, preferably 5–20 wales per inch width, and not more than 25 courses per inch length.

Figure 2:
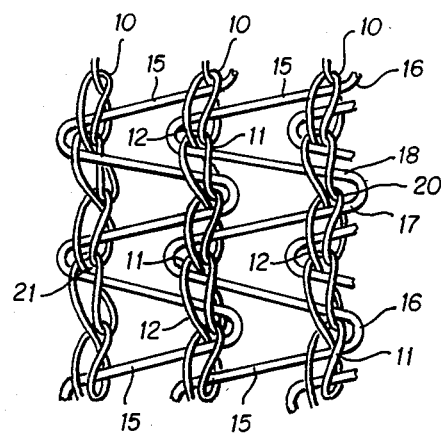
FIG. 2 is an exploded partial view of the preferred knit carrier of this invention.

More particularly, FIG. 2 shows reference numbers 10 indicating a series of parallel chains formed on conventional equipment. Each chain 10 is formed of a series of needle loops 11 drawn one through the other in succession. Floats or ties 12 connect the end of one needle loop with the beginning of the next. Each row of simultaneously formed and oppositely disposed needle loops in the cross direction of the fabric is designated by the term "course". That is, in FIG. 2, there are shown five courses of needle loops. It will be noted that each of the needle loops of FIG. 2 is formed in the same direction, that is, by movement of the thread from left to right over the needle.

Sinuous fill threads are indicated at 15. The fill threads 15 are looped between different chains in the fabric, the loops being formed around a link of one of the chains, and then around a link of another of the chains, each loop 16 of each fill thread 15 being in a course different from the course in which the other loopings thereof occur. In the FIG. 2 construction, the fill thread, after looping itself around a link in one chain, moves over to the link in the next course of the adjoining chain, and then back to the first chain two courses removed from the previous link in the first chain. It will be noted further that, moving from bottom to top of the figure, the leading part 17 of each thread loop 16 is bound in between a thread loop and a float of that course. Following part 18 of the same thread loop is bound in between the thread loop of the following couse in the same chain. The focal point of action of thread loop 16 on a chain is, therefor, the point 20 at which two chain loops meet.

As the fabric of FIG. 1 is stretched walewise, the chain loops tend to tighten and are relatively inextensible. However, if the fabric is stretched in the crosswise direction, the thread loops which point to the right will tend to distort the focal points 20 between adjacent chain loops to the left. The thread loops which point to the left, however, will act upon focal chain points 21, one course removed from focal chain points 20, so as to urge points 21 in the same course the entire width of the fabric toward the right. Any given chain, therefore, will be distorted in a zigzag fashion, first to the left, by the loops pointing to the right, and one course further on, to the right by the thread loops pointing to the left. The overall effect will be a stretching of the fabric widthwise and some contraction, lengthwise.

One significant advantage of the knit shown in FIG. 2 arises by reason of the fact that the fill threads 15 are bound in by the chains, as described above. When the fabric is cut, whether longitudinally, tranversely or diagonally, raveling, such as is characteristics of woven or usually knitted goods, will be minimized or entirely absent due to this binding-in feature.

Polymer Composition

The polymer composition coated on the carrier, described above, comprises a polyurethane prepolymer which is moisture curable, i.e., reacts with water at room temperature to form a cured product. The polymer composition must be easily coated onto the fabric, yet not subsequently flow off the fabric, must have good shelf life stability, be catalyzed by water, must react quickly, without high exotherm, to product physical phenomena, such as high tack followed by a quick cure to a very strong and tough polymer.

It has now been found that a polymer composition having the requisite properties can be obtained using a polyurethane prepolymer which is the reaction product of a polyalkylene ether diol, a polyalkylene ether triol and a modified diisocyanate.

Particularly preferred as the diols and triols are those based on polypropylene ethers, i.e.

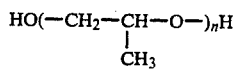

polypropylene ether diol; and

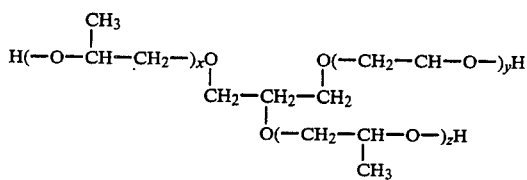

polypropylene ether triol, wherein n, x, y and z indicate the degree of polymerization. Suitable diols and triols are commercially available under trade names Pluracol P-1010 (BASF Wyandotte) and NIAX Polyol LG-650 (Union Carbide Corp.), respectively.

The modified diisocyanate is a mixture of 4,4'-methyl diphenyl diisocyanate (MDI) and MDI modified with carbodiimide. The reaction proceeds as follows:

A

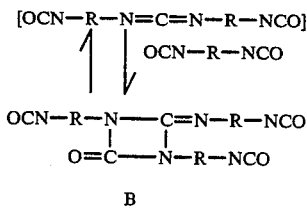

B where R is

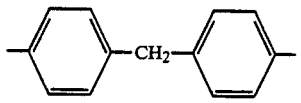

The mixture of A and B constitutes the modified diisocyanate. Such a modified diisocyanate is commercially avialable under the trade name Isonate 143-L (Upjohn Polymer Chemicals). The polypropylene ether diol may have an equivalent weight of 250–1500, preferably around 500. The polypropylene ether triol may have an equivalent weight of 84–1000 preferably around 84. The ratio of diol to triol may vary from 1:9 to 9:1, preferably around 6:4. The ratio of isocyanate to hydroxyl may be from 5:1 to 1.8/1, preferably around 3:1. A preferred prepolymer is formed by reacting the polypropylene ether diol, polypropylene ether triol and modified diisocyanate in the ratio of 0.6/0.4/3.0 respectively, all the above ratios by equivalents.

The reaction of the above-noted components in a ratio of 1 equivalent of total polyol (diol plus triol) to more than 2 equivalents of modified diisocyanate yields an NCO-terminated prepolymer. The viscosity of the prepolymer may be controlled, by techniques well-known in the polymer art, so as to obtain a prepolymer that is coatable upon the substrate. A plasticizer may be employed to facilitate coatablity, but should not be present in amounts greater than 25% by weight of the polyurethane prepolymer composition. Suitable plasticizers are commercially available, e.g., Rucoflex DOA (Hooker Chemical Corp.)

Once prepolymer formation is complete, the prepolymer is then mixed with an amine catalyst, especially a tertiary amine catalyst, that will react quickly to form the cured polyurethane polymer when subsequently exposed to water. The curing reaction, when exposed to water, will take place as follows:

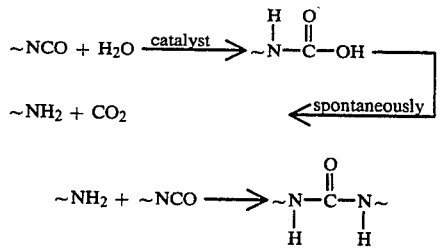

Suitable catalysts are well-known in the polyurethane art and are commercially available. Particularly preferred as a catalyst is the compound [(CH$_3$)$_2$NCH$_2$CH$_2$]$_2$O, available commercially as an amine-glycol mixture under the trade name NIAX Catalyst A-1 (Union Carbide Corp.) The catalyst is added in an amount of 0.1 to 1.0% by wt based on the prepolymer composition. Most preferably the catalyst is added in an amount less than 0.4% by wt of the prepolymer composition.

Additives to the prepolymer composition have also been found useful in controlling the properties to produce an optimum formulation for coating and cast forming.

A thixotropic agent has been found desirable to eliminate resin flow from the coated web upon long-term standing in the package. Such thixotropic agents are well-known in th art and are commercially available. Particularly preferred in this respect is fumed silica, available commercially, e.g., under the trade name M-5 Cab-O-Sil (Cabot Corp.) This may be added in amounts of 0.5 to 4.0% by wt, preferably 2.0% by wt.

An antifoam agent insures that the resin is not blown into a foam by its own CO$_2$ generation. Such antifoam agents are well-known in the art and are commercially available. Particularly preferred in this respect are the silicone based antifoamants, available commercially, e.g., under the trade name Antifoam-A (Dow Corning Corp.) This may be added in amounts of 0.25 to 2.0% by wt based on the prepolymer composition, most preferably 1.0% by wt.

A pH adjustment agent, i.e., increased acidity, improves shelf life stability. Suitable acids may be added in this respect, e.g., mineral acids. Particularly preferred is phosphoric acid. This may be added in amounts of 0.01 to 1.0% by wt based on the prepolymer composition, most preferably less than 0.3% by wt.

Method of Making Orthopedic Cast Forming Bandage

Figure 3:
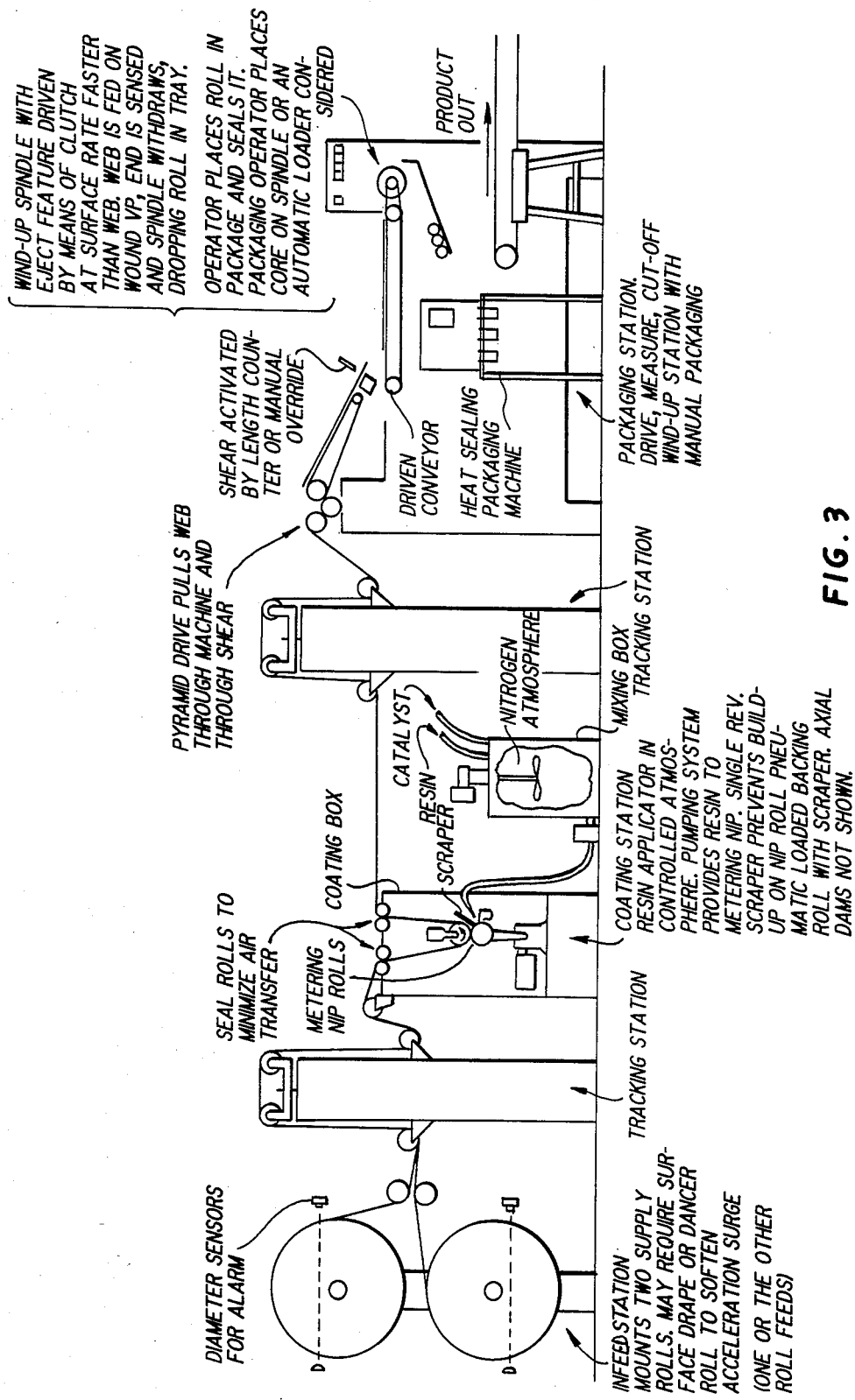
FIG. 3 is a schematic view of a method of fabricating a resin coated bandage embodying this invention.

Turning now to FIG. 3, an infeed station is provided wherein two rolls of the appropriate knitted webbing are provided. One roll feeds to the production line, while the other is held ready for changeover, i.e., splicing, when the first roll is exhausted. After one roll is exhausted, changeover to the other roll takes place, and the exhausted roll is replaced with a new roll to await the next changeover. Diameter sensors, e.g., a photoelectric system, are provided for each roll to alert operating personnel to an impending changeover. A surface brake or a dancer roll (neither shown) can be provided to soften the acceleration surge upon resumption of production.

The web then passes through a tracking station, for the maintenance of tension on the web, to the coating station where the catalyzed polymeric composition is coated on the web. The coating station is a sealed box wherein the atmosphere is controlled to a maximum of one hundred (100) parts per million (PPM) of moisture. Entrance and egress of the web to and from the coating station is controlled by seal rolls to minimize air transfer. Coating is achieved by passing the web through a set of metering nip rolls equipped with a single reverse scraper to prevent resin build-up on the nip roll. Resin is fed to the nip rolls, from a mixing vessel outside the coating station, through a conduit vessel outside the coating station, through a conduit equipped with a variable speed pump. The mixing vessel comprises a sealed tank equipped with a stirrer and maintained under a dry nitrogen atmosphere, wherein the resin comprising the polyurethane prepolymer and the additives is mixed with the amine catalyst prior to coating.

From the coating station, the coated web then passes through another tracking station and then to a pyramid drive which supplies the power for pulling the web through the machinery. From the pyramid driven, the coated web is laid on a driven conveyor belt and fed to a shearing device, e.g., a knife blade, which cuts the web into predetermined lengths or can be manually overridden at the convenience of the operator for special production purposes. The cut lengths of coated web are then fed to a second driven conveyor which feeds the cut lengths to a wind-up spindle. The wind-up spindle draws the cut lengths of web into a tight roll by rotating at a linear speed greater than that of the driven conveyor. When the end of the cut length of web is sensed, the spindle is withdrawn and the roll drops to a receiving tray. The tight rolls of coated web are then packaged in a container to protect the web from atmospheric moisture, e.g., a laminated foil package or a hermetically sealed container.

As is obvious from the water-sensitive nature of the polymer composition, the entire production line is maintained in a tightly controlled low moisture environment. While the resin-coated web can be exposed to 65% relative humidity for about one minute without detrimental effect, several minutes of exposure produces a skin on the polymer, therefore lower humidity is preferable and, most preferably, a moisture content paralleling that of the enclosed coating station (about 100 PPM) is used.

Additionally, it is desirable to precondition the fabric carrier to obtain a low moisture content therein, prior to entrance into the coating process. This may be achieved by allowing the fabric to stand in a controlled humidity environment (50% relative humidity or less) for about a week or more. Moreover, proper selection of the fabric material can further alleviate moisture problems, e.g., the preferred polyethyleneterephthalate fiber has a moisture pick-up of less than 0.5% by weight, after drying and subsequent exposure to 65% relative humidity at room temperature.

Orthopedic Cast Forming Bandage and Use Thereof

A typical bandage formed form the coated web manufactured according to the process hereinabove described with reference to FIG. 3 may be approximately 6–12 feet long and 2–6 inches wide.

In using the bandage to make an orthopedic cast it is convenient to simply immerse the rolled bandage in a vessel of the tap water for a period of generally less than 2 minutes, preferably, less than 1 minute. Other methods of wetting, e.g., spraying could be used, but a water bath is preferable for rapid and uniform contacting of all areas of the bandage. When removed from the water, the bandage can be readily wrapped about a limb wherein the normal underlying stockinette or padding is employed. The bandage can be twisted, gathered, formed, re-formed, molded rolled and unrolled as desired, there being ample time for the bonding between adjacent layers and the formation of the cast. The molding-working time (tack free) for the practitioner is typically 3–5 minutes, however, this can be varied by variation of the catalyst content of the polymer composition. Likewise, the hardening time will vary with catalyst content typically being 5–15 minutes. Moreover, the cast becomes weight bearing within about 30 minutes of application. The curing of the cast results in only a slight exotherm which causes no discomfort to the patient.

The resulting cast has a number of desirable features. It is sufficiently transparent to X-rays so that close to skin quality X-rays can be achieved. This means lower X-ray voltage may be employed as compared to other cast materials, such as plaster. The case is lightweight and a strong structure can be achieved with as little as two layers of the material. Channels are retained, so that the skin is able to breathe through the cast and maceration over the normal period of time for which the cast is worn is not observed. Strong bonding is obtained between the layers of the webbing, so that the case does not come apart. In addition, the cast can be immersed in water and because of the porosity of the cast, the water will evaporate and the skin underneath the cast will retain its healthy condition. The heavy strands of the fabric web provide structure to the material and remain in place when positioned, so as to insure that on hardening the immobilized limb is held in the desired position.

During use, the cast has good wet strength and does not deteriorate upon repeated immersions in water, such as during swimming or taking showers or baths. In addition, the cast is abrasion resistant and capable of sustaining substantial impact. The cast provides protection for the injured limb and can be used in most situations normally encountered by the wearer. Finally, the cast is readily removable by conventional means such as by cutting with a conventional vibrating sawtooth disc.

It will be appreciated that the term orthopedic "casts" as used herein is also means to include, where applicable, the forming of splints and braces.

Having now fully described this invention, it will be apparent to one of ordinary skill in the art that many changes and modifications can be made thereto without departing from the spirit or scope of the invention set forth herein.

What is claimed as new and desired to be secured by Letters Patent of the United States is:

1. A bandage material for forming in place an orthopedic cast comprising a pliant, large mesh fabric carrier formed from a knot of a high-strength, high-modulus fiberglass yarn with a low moisture pick-up, the fabric carrier having openings of relatively large transverse dimension, and being coated with a polymer composition comprising (a) a water curable polyurethane prepolymer comprising the reaction product of a polyalkylene ether diol, a polyalkylene ether triol and a diisocyanate, wherein the ratio of diol to triol is from 1:9 to 9:1 and (b) an amine catalyst.

2. The bandage material according to claim 1, wherein the polymer composition further comprises a mineral acid.

3. The bandage material according to claim 2, wherein the mineral acid is phosphoric acid.

4. The bandage material according to claim 1, wherein the amine catalyst is a tertiary amine.

5. The bandage material according to claim 4, wherein the tertiary amine is $[(CH_3)_2NCHCH_2]_2O$.

6. The bandage material ccording to claim 1, wherein one equivalent of polyol (diol and triol) is reacted with more than 1.8 equivalents of isocyanate.

7. The bandage material ccording to claim 1, wherein the polyurethane prepolymer comprises the reaction product of polypropylene ether diol, polypropylene ether triol and a diisocyanate.

8. The bandage material according to claim 7, wherein the diisocyanate is a modified diisocyanate prepared by reacting a diisocyanate with less than a stoichiometric amount of carbodiimide.

9. The bandage material according to claim 8, wherein the modified diisocyanate is a mixture of OCN—R—NCO, and

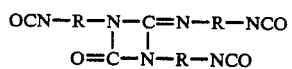

where R is

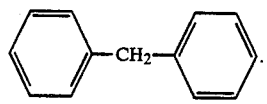

* * * * *